United States Patent [19]
Crainich

[11] Patent Number: 5,976,160
[45] Date of Patent: Nov. 2, 1999

[54] HANDLE MECHANISM WITH TWO DISTINCT PIVOT POINTS

[75] Inventor: Lawrence Crainich, Charlestown, N.H.

[73] Assignee: Design Standards Corporation, Charlestown, N.H.

[21] Appl. No.: 09/052,298

[22] Filed: Mar. 31, 1998

[51] Int. Cl.[6] .................................................. A61B 17/04
[52] U.S. Cl. .......................................... 606/142; 606/143
[58] Field of Search .................................... 606/142, 143, 606/1; 227/19

[56] References Cited

U.S. PATENT DOCUMENTS

| | | | |
|---|---|---|---|
| 4,664,305 | 5/1987 | Biake et al. ................................ | 227/19 |
| 5,258,010 | 11/1993 | Green et al. .............................. | 606/219 |
| 5,382,254 | 1/1995 | McGarry et al. ........................ | 606/143 |
| 5,542,949 | 8/1996 | Yoon ......................................... | 606/143 |
| 5,573,541 | 11/1996 | Green et al. .............................. | 606/143 |
| 5,601,573 | 2/1997 | Fogelberg et al. ....................... | 606/143 |
| 5,607,436 | 3/1997 | Pratt et al. ................................ | 606/143 |

*Primary Examiner*—Gary Jackson
*Attorney, Agent, or Firm*—Bachman & Lapointe, P.C.

[57] ABSTRACT

A handle assembly for a medical instrument having at least one member moveable in at least a first direction against a first bias and a second direction against a second bias stronger than the first bias, includes a housing, a trigger operatively associated with the at least one member and pivotably mounted relative to the housing for pivot around a first limited pivot point and a second pivot point, the trigger being pivotable relative to the housing between a rest position and a pivoted position, wherein pivot of the trigger relative to the housing from the rest position toward the pivoted position results in pivot first around the first limited pivot point and movement of the at least one member in the first direction against the first bias, and subsequently in pivot around the second pivot point and movement of the at least one member in the second direction against the second bias.

10 Claims, 3 Drawing Sheets

5,976,160

HANDLE MECHANISM WITH TWO DISTINCT PIVOT POINTS

BACKGROUND OF THE INVENTION

The invention relates to a handle mechanism and, more particularly, to a handle mechanism for operating a medical instrument to provide sequential movement of different elements, or sequential movement in different directions of the same element.

In the field of medical instruments, it is frequently desirable to provide sequential operations such as, for example, the positioning of a surgical staple or clip from a magazine to an application area of the instrument, followed by operation of the instrument to actually apply the staple or clip. Further, depending upon the device, some elements of the instrument may need to be moved out of the path of movement of other elements to allow completion of a desired operation. In the course of use of a surgical instrument such as those set forth above, it is awkward and undesirable to perform such sequential operations using different control members for each function.

It is therefore the primary object of the present invention to provide a handle mechanism for a medical instrument which provides for smooth and sequential operation of various elements of a medical instrument using a single control member.

It is a further object of the present invention to provide a handle mechanism for a medical instrument wherein sequential operations are carried out using a single control member operable with only the hand.

It is still another object of the present invention to provide a handle mechanism for carrying out one-handed sequential operations wherein the handle mechanism is simple in manufacture and operation.

It is still another object of the present invention to provide a medical instrument incorporating the handle mechanism of the present invention.

Other objects and advantages of the present invention will appear hereinbelow.

SUMMARY OF THE INVENTION

In accordance with the present invention, the foregoing objects and advantages have been readily attained.

According to the invention, a handle assembly for a medical instrument having at least one member moveable in at least a first direction against a first bias and in a second direction against a second bias stronger than the first bias is provided, which handle assembly comprises: a housing; a trigger operatively associated with said at least one member and pivotably mounted relative to said housing for pivot around a first limited pivot point and a second pivot point, said trigger being pivotable relative to said housing between a rest position and a pivoted position, wherein pivot of said trigger relative to said housing from said rest position toward said pivoted position results in pivot first around said first limited pivot point and movement of said at least one member in said first direction against said first bias, and subsequently in pivot around said second pivot point and movement of said at least one member in said second direction against said second bias.

In further accordance with the invention, a medical instrument is provided, comprising a housing; at least two drive members, a first drive member of said at least two drive members being slidable against a first bias, and a second drive member of said at least two drive members being slidable against a second bias stronger than said first bias; and a trigger operatively associated with said at least two drive members and pivotably mounted relative to said housing for pivot around a first limited pivot point and a second pivot point, said trigger being pivotable relative to said housing between a rest position and a pivoted position, wherein pivot of said trigger relative to said housing from said rest position toward said pivoted position results in pivot first around said first limited pivot point and movement of said first member against said first bias, and subsequently in pivot around said second pivot point and movement of said second member against said second bias.

BRIEF DESCRIPTION OF THE DRAWINGS

A detailed description of preferred embodiments of the present invention follows, with reference to the attached drawings, wherein.

DETAILED DESCRIPTION

The invention relates to a handle assembly for a medical instrument, especially a handle assembly for a medical instrument which, in use, requires sequential movement of one or more members or elements. The handle assembly is especially for use with an instrument which has at least one member moveable in a first direction against a first bias and a second direction against a second bias which is different than the first bias.

Figure 1:
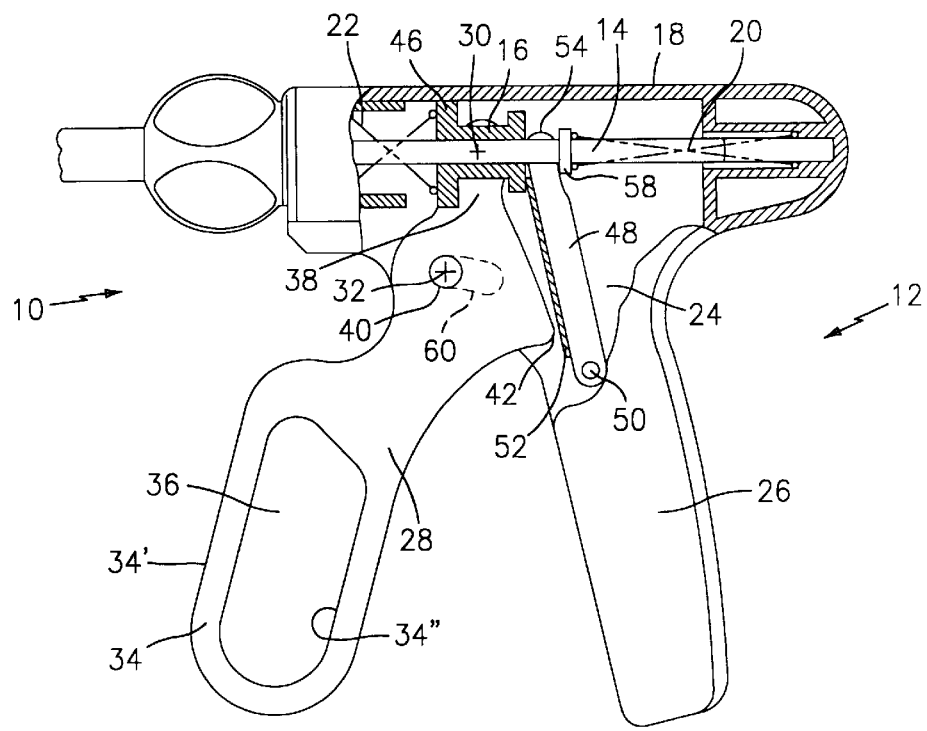
FIG. 1 illustrates a side sectional view of a medical instrument including a handle assembly according to the present invention.

Referring to the drawings, FIG. 1 shows a partially sectional view of a medical instrument 10 having a handle assembly 12 in accordance with the present invention. In the embodiment illustrated in FIG. 1, medical instrument 10 has a first member 14 which may, for example, correspond to a driver for a transfer mechanism to position a surgical staple or clip (not shown) in a ready position, or to position the transfer mechanism itself out of the way of other elements, and a second member 16, which may for example be a drive member for applying or "firing" a staple or clip positioned in the ready position. First and second members 14, 16 are slidable or moveable within a housing 18 against first and second bias members 20, 22 such as springs or the like.

As set forth above, it is frequently desirable in the use of a medical instrument for at least one member or element such as members 14, 16 to be moveable sequentially, and it is further desirable for this operation to be carried out in a smooth and non-encumbering manner. In accordance with the present invention, handle assembly 12 provides for smooth, sequential movement of members 14, 16 as desired in a one-handed and simple operation.

Still referring to FIG. 1, handle assembly 12 in accordance with the present invention preferably includes a housing 24 which may be an extension of housing 18 for first and second members 14, 16 as shown, and which preferably has a downwardly depending handle or pistol grip 26. Handle assembly 12 also preferably includes a trigger member 28 pivotably mounted relative to housing 24 for pivot around a first limited pivot point 30 and a second pivot point 32. Pivot around first and second pivot points 30, 32 and subsequent motion of members 14, 16 will be further discussed below.

Figure 3:
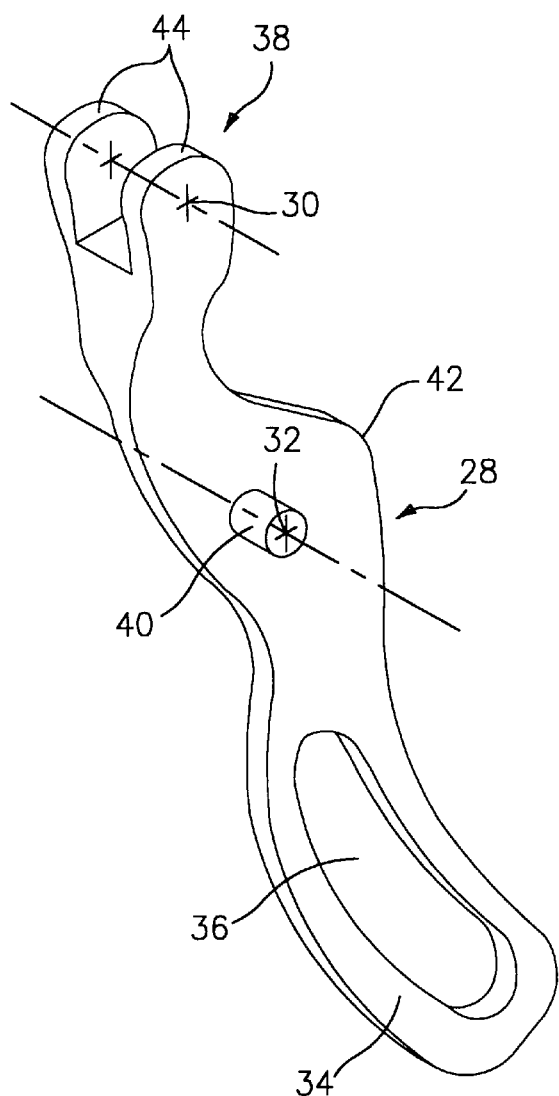
FIGS. 3 and 3a illustrate preferred embodiments of a trigger element of the handle assembly of the present invention.

Still referring to FIG. 1, and referring also to FIG. 3, trigger 28 preferably includes a finger grip portion 34 which is preferably positioned for easy grip of both pistol grip member 26 and finger grip portion 34 in a single-handed manner with one or more fingers engaging finger grip portion 34 while the palm area of the hand, and possibly a thumb portion of the hand, engages pistol grip portion 26. Finger portion 34 may suitably have a cutout area 36 as shown to provide several different surfaces 34', 34" against which fingers can be engaged to provide a means for opening the trigger in the event of a jam.

Trigger 28 preferably also includes a head portion 38 adapted to engage second member 16, an axle 40 which is pivotably mounted in housing 18 as will be discussed below, and a substantially rearwardly projecting cam member 42.

As best shown in FIG. 3, head portion 38 may suitably have a yoke structure including two substantially parallel tabs or arms 44 extending to engage on either side of second member 16, which may preferably be provided in the form of a spool having flanges 46 for engaging on either side of head portion 38. This structure of head portion 38 and second member 16 advantageously allows for the pivotable engagement of head portion 38 with second member 16 so as to provide a first limited pivot point 30 for pivot of trigger 28 relative to second member 16/housing 24.

An additional pivot arm or member 48 is also preferably provided, and pivotably mounted relative to housing 24, for example at hinge 50. Additional pivot 48 is preferably provided in the form of a substantially elongate arm having a central portion 52 which is engaged by cam member 42 of trigger 28, and a head portion 54 engaging first member 14.

Head portion 54 of additional pivot member 48 is preferably also adapted to engage with first member 14, preferably with a yoke or upstanding arm structure similar to head portion 38 of trigger 28. Head portion 54 serves to engage against a flange 58 of first member 14 so as to transmit motion of additional pivot member 48 to first member 14 as desired and as will be further described below.

Housing 18 preferably further includes an arcuate groove 60 for slidably receiving axle 40 of trigger 28. Arcuate groove 60 is preferably provided having the shape of a segment of a circle preferably having a center coincident with first limited pivot point 30 as shown. In this manner, when trigger 28 is pivoted around first limited pivot point 30, axle 40 slides within arcuate groove 60. Furthermore, arcuate groove 60 defines the limits of pivot allowed around first limited pivot point 30. Axle 40 and arcuate groove 60 further serve to define second pivot point 32 as shown.

Figure 2:
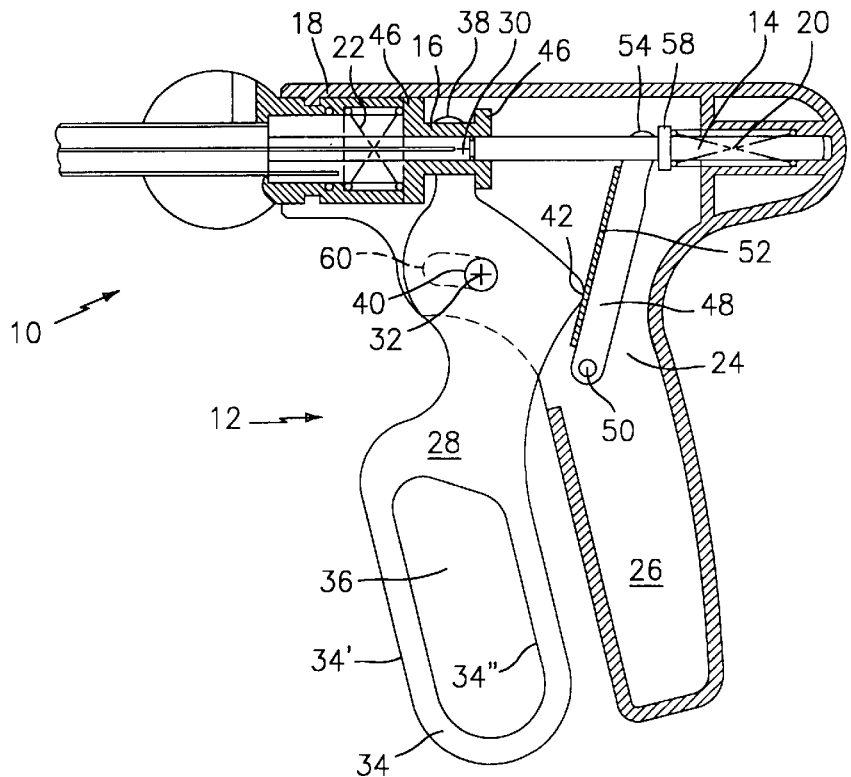
FIG. 2 illustrates the medical instrument of FIG. 1 with the handle assembly in a pivoted position.

As set forth above, first and second members 14, 16 are biased by first and second bias members 20, 22. It is preferred that second bias member 22 be stronger in force than first bias member 20. With this configuration when trigger 28 is pivoted toward pistol grip member 26 from the extended or rest position illustrated in FIG. 1, pivot initially occurs around first limited pivot point 30, with axle 40 sliding along arcuate groove 60 and cam member 42 contacting and thereby pivoting additional pivot member 48 such that first member 14 is rearwardly biased against bias member 20 toward the position as shown in FIG. 2. When axle 40 reaches the rearward end 62 of arcuate groove 60, further pivot of trigger 28 around first limited pivot point 30 is prevented by the structure of axle 40 and groove 60, and the pivot of the trigger shifts from point 30 to point 32. Further pivot of trigger 28 results in pivot around second pivot point 32, with head portion 38 pushing second member 16 in a substantially forward direction against the stronger bias of second bias member 22. Thus, pivot of trigger 28 from the rest position of FIG. 1 to the fully pivoted position of FIG. 2 results in sequential movement of first member 14, and then second member 16, as desired.

As set forth above, handle assembly 12 could, for example, be associated with a surgical staple or clip applicator wherein the first member 14 is a driver for a transfer mechanism for positioning a staple or clip between closing anvils of the device (not shown), and wherein second member 16 is a driver for operating the closing anvils and thereby applying the staple or clip as desired.

Upon completion of this operation, it should readily be appreciated that release of trigger 28 results in pivot of trigger 28 driven indirectly by bias members 20, 22 from the pivoted position of FIG. 2 to the extended or rest position of FIG. 1. Further, it should be appreciated that movement of first and second members 14, 16 during return of trigger 28 to the rest position occurs in a reverse sequential order. Thus, return pivot will occur first around second pivot point 32 with second member 16 returning to the position of FIG. 1, and pivot will subsequently take place around limited pivot point 30 with additional pivot member 48 and first member 14 returning to the position of FIG. 1.

Although the above description is given in terms of use with a surgical stapler or clip applicator, it should readily be appreciated that handle assembly 12 in accordance with the present invention would be ideally suited to any type of medical instrument wherein one or more members are moveable in one or more different directions, and such movement is desirable to be effected in a sequential manner.

It should also be appreciated that during pivot around first limited pivot point 30, second pivot point 32 moves through arcuate groove 60, and during pivot around second pivot point 32, first limited pivot point 30 moves along with trigger head portion 38 and second member 16. Pivot point 30 is referred to as a limited pivot point because the structure of axle 40 and groove 60 serves to define a limited range of pivot around point 30.

Also, although this disclosure is presented in terms of the preferred embodiment related to sequential movement of separate members 14, 16 in different directions, it can also provide sequential movement in the same direction, and it is also well within the scope of the invention to use handle assembly 12 with an instrument so as to provide sequential operation of a single member or element, for example moved through several different maneuvers.

Figure 4:
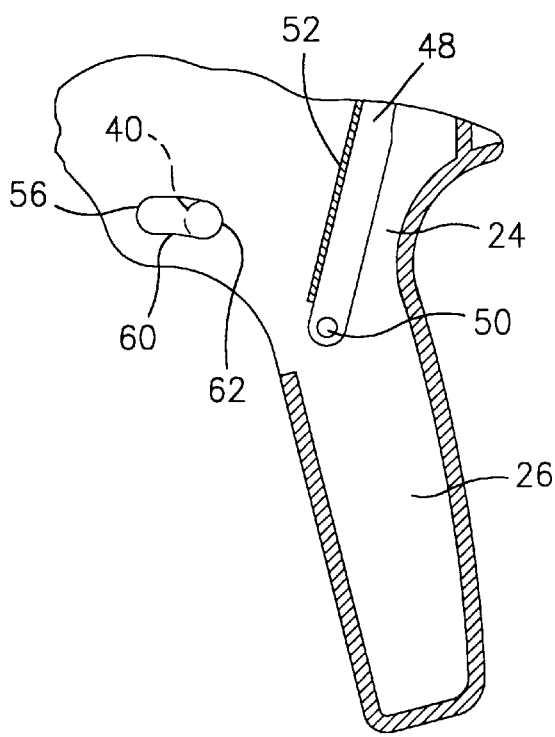
FIGS. 4 and 4a illustrate a portion of preferred embodiments of a housing element of the handle assembly in accordance with the present invention.

FIGS. 3 and 4 further illustrate certain elements of handle assembly 12 in accordance with the present invention. As discussed above, FIG. 3 shows a perspective view of trigger 28 having head portion 38, axle 40, and finger grip portion 34 as described.

FIG. 3 also further illustrates preferred positioning of first limited pivot point 30 and second pivot point 32 such that they are defined spaced along a length of trigger 28, which positioning further provides for a smooth and efficient operation of instrument 10 in accordance with the present invention.

FIG. 4 shows a portion of housing 18 including arcuate groove 60 for receiving axle 40 and having forward end 56 and rearward end 62 for limiting the range of movement of axle 40 in groove 60. Also, the drawings are sectional views and show only one side of housing 24. Of course, axle 40 would preferably extend from both sides of trigger 28 to engage with grooves 60 on each side of housing 24 to provide a stable assembly.

Figure 3A:
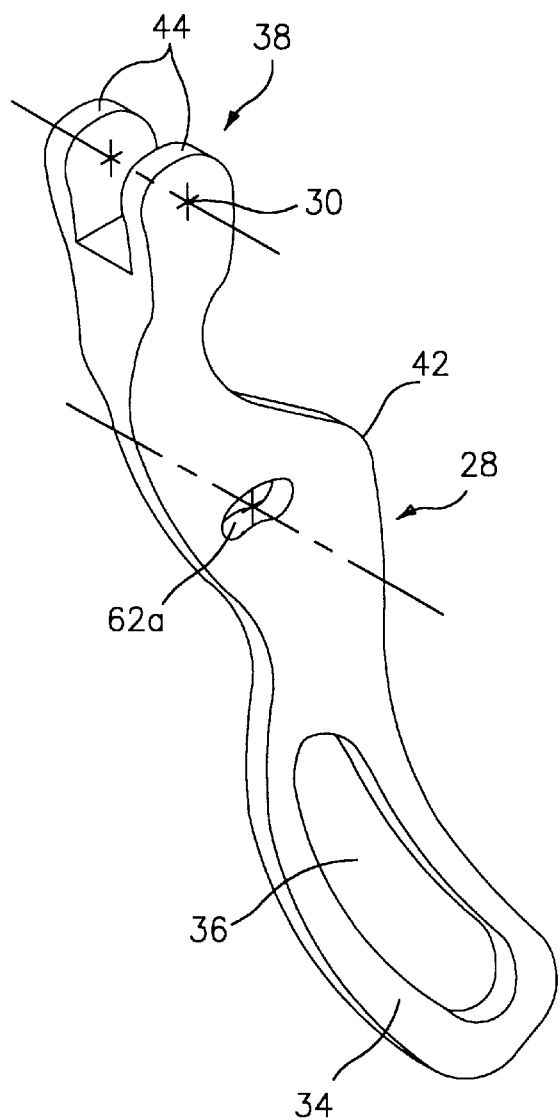
Figure 4A:
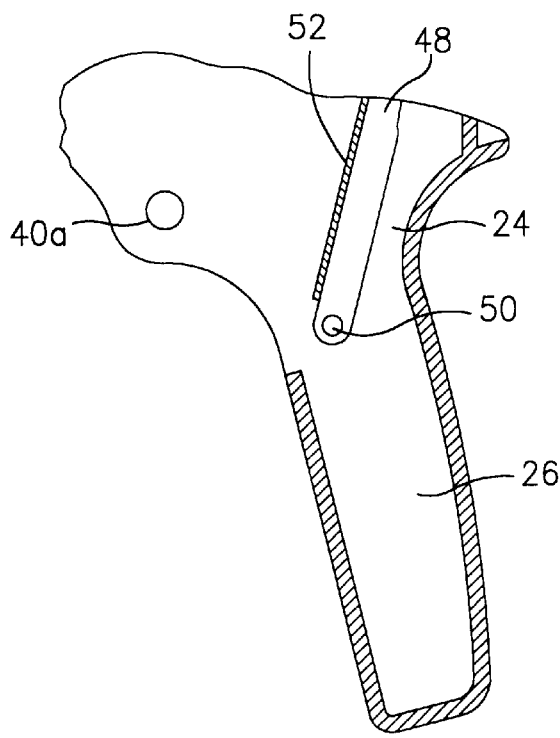

Referring now to FIGS. 3a and 4a, it should readily be appreciated that although this disclosure is made in terms of axle 40 being positioned on trigger 28, and arcuate groove 60 being positioned on housing 24, these elements could of course be reversed, with an arcuate groove 60a (FIG. 3a) being positioned on trigger 28 and an axle 40a (FIG. 4a) mounted in housing 24, well within the scope of the present invention.

It should also be readily appreciated that use of handle assembly 12 in accordance with the present invention advantageously provides for one-handed operation of a medical instrument so as to provide sequential operation of one or more elements or members in one or more directions or maneuvers.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A handle assembly for a medical instrument having at least one member moveable in at least a first direction against a first bias and a second direction against a second bias stronger than said first bias, comprising:

a housing;

a trigger operatively associated with said at least one member and pivotably mounted relative to said housing for pivot around a first limited pivot point and a second pivot point, said trigger being pivotable relative to said housing between a rest position and a pivoted position, wherein pivot of said trigger relative to said housing from said rest position toward said pivoted position results in pivot first around said first limited pivot point and movement of said at least one member in said first direction against said first bias, and subsequently in pivot around said second pivot point and movement of said at least one member in said second direction against said second bias.

2. A handle assembly according to claim 1 wherein said first pivot point is defined by a pivotable association of said trigger with said at least one member, and wherein said second pivot point is defined by an axle mounted on one of said trigger and said housing and a substantially arcuate groove positioned on the other of said trigger and said housing, said axle being slidably positioned in said groove whereby pivot of said trigger around said first limited pivot point slides said axle in said groove, and wherein said groove defines a range of pivot around said first limited pivot point.

3. A handle assembly according to claim 2, wherein said arcuate groove is defined on said housing, and said axle is fixed to said trigger.

4. A handle assembly according to claim 2, wherein said arcuate groove defines a segment of a circle having a center substantially coincident with said first pivot point.

5. A handle assembly according to claim 1, wherein said housing comprises a pistol grip member, and wherein said trigger comprises a substantially elongate member pivotable relative to said pistol grip member.

6. A handle assembly according to claim 5 wherein said first limited pivot point and said second pivot point are spaced along a length of said trigger.

7. A medical instrument, comprising:

a housing;

at least two drive members, a first drive member of said at least two drive members being slidable against a first bias, and a second drive member of said at least two drive members being slidable against a second bias stronger than said first bias; and a trigger operatively associated with said at least two drive members and pivotably mounted relative to said housing for pivot around a first limited pivot point and a second pivot point, said trigger being pivotable relative to said housing between a rest position and a pivoted position, wherein pivot of said trigger relative to said housing from said rest position toward said pivoted position results in pivot first around said first limited pivot point and movement of said first member against said first bias, and subsequently in pivot around said second pivot point and movement of said second member against said second bias.

8. An instrument according to claim 7, wherein said trigger has a head portion contacting said second drive member, and a cam portion associated with said first drive member.

9. An instrument according to claim 8, further comprising a pivot arm pivotably mounted relative to said housing and contacting said first drive member and said cam portion, whereby pivot of said trigger around said first pivot point results in pivot of said pivot arm and movement of said drive member.

10. An instrument according to claim 9 wherein said first drive member is mounted and slidable substantially parallel relative to said second drive member.

* * * * *